United States Patent [19]
Arca et al.

[11] Patent Number: 6,103,915
[45] Date of Patent: Aug. 15, 2000

[54] PROCESS FOR THE PREPARATION OF OLEFINIC EPOXIDES

[75] Inventors: Vittorio Arca, Chioggia; Piero Furlan, Treviso; Roberto Buzzoni, S. Mauro Torinese, all of Italy

[73] Assignee: Enichem S.p.A., S. Donato Mil.se, Italy

[21] Appl. No.: 09/222,875

[22] Filed: Dec. 30, 1998

[30] Foreign Application Priority Data

Jan. 15, 1998 [IT] Italy .................................. MI98A0053

[51] Int. Cl.⁷ ...................... C07D 301/12; C07D 301/19
[52] U.S. Cl. ............................................................ 549/531
[58] Field of Search .............................................. 549/531

[56] References Cited

U.S. PATENT DOCUMENTS

| | | | |
|---|---|---|---|
| 5,412,122 | 5/1995 | Saxton et al. | 549/531 |
| 5,675,026 | 10/1997 | Thiele | 549/531 |
| 5,859,265 | 1/1999 | Mueller et al. | 549/531 |

FOREIGN PATENT DOCUMENTS

| | | |
|---|---|---|
| 0 230 949 | 8/1987 | European Pat. Off. . |
| 0 712 852 | 5/1996 | European Pat. Off. . |
| 757 043 | 2/1997 | European Pat. Off. . |
| 4 425 672 | 1/1996 | Germany . |
| 196 00 708 | 7/1997 | Germany . |
| 2 309 655 | 8/1997 | United Kingdom . |

*Primary Examiner*—Ba K. Trinh
*Attorney, Agent, or Firm*—Oblon, Spivak, McClelland, Maier & Neustadt, P.C.

[57] ABSTRACT

Process for the production of epoxides by the reaction of at least one olefin and hydrogen peroxide, or a compound capable of producing hydrogen peroxide under the reaction conditions, in the presence of a catalyst consisting of titanium silicalite subjected to ion exchange treatment with metal cations ($M^{n+}$) present on the catalyst in a quantity ranging from 0.01 to 1% by weight with respect to the total weight.

26 Claims, No Drawings

PROCESS FOR THE PREPARATION OF OLEFINIC EPOXIDES

The present invention relates to a process for the production of olefinic epoxides.

More specifically, the present invention relates to a process for the production of olefinic epoxides by the reaction of olefins and hydrogen peroxide, or compounds capable of producing hydrogen peroxide under the reaction conditions, in the presence of a titanium-silicalite catalyst, subjected to treatment with metal cations.

Olefinic epoxides or oxides are intermediates which can be used for the preparation of a wide variety of compounds. For example, epoxides can be used for the production of glycols, condensation polymers such as polyesters or for the preparation of intermediates used in the synthesis of polyurethane foams, elastomers, seals, etc.

Numerous processes for the preparation of olefinic oxides are known in the art. For example, European patent EP 100.119 describes a process for the preparation of epoxides by the reaction between an olefin and hydrogen peroxide, or a compound capable of producing hydrogen peroxide under the reaction conditions, in the presence of titanium silicalite. These catalysts enable epoxides to be obtained with a high selectivity.

The acidity which characterizes these catalysts, however, even if low, is sufficient to activate consecutive solvolytic reactions on the epoxide with the opening of the ring. This results in an increase in production costs owing to the decrease in the yield to epoxide and for the separation of the by-products formed.

European patent EP 230.949 describes a process for the preparation of epoxides from olefins and hydrogen peroxide which uses as catalyst a titanium silicalite treated, before or during the epoxidation reaction, with an agent which neutralizes the acidity of the catalyst itself. Neutralizing agents indicated are organic derivatives of silicon of the type $XSiR_3$ (X=halogen, for example) or hydrosoluble substances deriving from cations of the Ist and IInd group, with a different basic strength.

In the case of treatment with organic derivatives of silicon, a great limitation consists in their well-known reactivity which makes it necessary to exclusively carry out a preventive treatment of the catalyst, as treatment effected during the epoxidation reaction, adding these compounds in continuous, would produce undesired reactions even with the solvents and reaction products.

With respect to the use of basic substances of cations of the Ist and IInd group, a great limitation lies in their hydrosolubility, making it necessary for there to be an amount of water in the reaction solvent, right from the beginning, which is such as to completely dissolve them if the neutralization treatment is to be carried out during the reaction.

On the other hand, it is well known that the physical solubilization of an olefin in a protic organic solvent, such as for example an alcohol, decreases with an increase in the water present. For example in the case of propylene, a few percentage units of water with respect to the weight of alcoholic solvent, drastically lower its solubility, requiring pressure conditions much higher than atmospheric values to keep the concentration of propylene dissolved in the reaction medium at the necessary values.

Published European patent application EP 712.852 (ARCO) describes the use of titanium silicalites in the presence of low concentrations of non-basic salts to increase the selectivity to epoxide apparently without there being a decrease in the conversion rate of hydrogen peroxide. The salts are those whose cations belong again to group I and II and whose anions are chloride, bromide, nitrate, sulfate and phosphates, arsenates, stannates, formiates, acetates (and higher carboxylates up to $C_{10}$) and bicarbonates. In the context of the ARCO process, these anions are considered as being non-basic because when they are dissolved to a concentration of 0.1 N, or in any case to saturation, in water at 25° C., solutions are obtained with pH<8 and, in any case not less than 4.

Significant results are not even obtained in this case, however, either in terms of conversion of hydrogen peroxide or, above all, selectivity to epoxide.

The Applicant has succeeded in finding a process which overcomes all the difficulties and limitations described above by adequately exploiting the capacity of titanium silicalite to exchange cations. In particular, it has been observed that this ion exchange treatment allows catalysts to be obtained which are capable of reaching substantially higher selectivities to epoxide than those with catalysts as such (not treated).

The present invention therefore relates to a process for the production of epoxides by the reaction of at least one olefin and hydrogen peroxide, or a compound capable of producing hydrogen peroxide under the reaction conditions, in the presence of a catalyst consisting of titanium silicalite subjected to ion exchange treatment (exchanged) with metal cations ($M^{n+}$) present on the catalyst in a quantity ranging from 0.0001 to 1% by weight with respect to the total weight.

According to the present invention therefore, owing to the unexpected exchange capacity of titanium silicalite and the versatility which characterizes an ion exchange operation, it is possible to carry out exchange treatment on the catalyst as such with cations on the acid centres of the catalyst itself, which results in a considerable reduction in its intrinsic acidity, which is mainly responsible in epoxidation reactions for the formation of by-products from the epoxide formed.

Any cation capable of reducing the intrinsic acidity of titanium silicalite can be used in the preparation of the catalyst of the process of the present invention. Examples of particularly preferred cations are metal cations of group IIB (in particular zinc); group IIIB (in particular lanthanium); the rare-earth group, or lanthanides, (with particular reference to samarium). Other examples are cations of vanadium (in particular as metavanadate ion); tungsten (mainly as metatungstate ion); tin and lead (with particular reference to the latter); indium and tallium (with particular reference to the latter); and, naturally, cations of group I and II, and ammonium.

These $M^{n+}$ cations can naturally be part of organic or inorganic salt complexes contemporaneously containing more than one of the cations of the above elements and associated with one or more of the elements selected from carbon, boron, silicon, nitrogen, phosphorous, sulfur, fluorine, selenium, arsenic, tin, molibden and antimonium.

Examples of organic or inorganic salt complexes that comprise $M^{n+}$ cations are: hexafluoroarsenates, hexafluoroantimonates, hexafluorophosphates, hexafluorostannates, trifluoromethanesulfonates, cyclohexabutyrrates, 2-ethylhexanates, ethylenediaminotetracetates, nitrilotriacetates, oxinates, cupferronates, alkyl or aryl or aralkylsulfates, trimethylsilylethanesulfonates, dithizonates, sulfosalicylates, acetylacetonates, etc.

From a process point of view, the ion exchange can be carried out with various techniques but those used in the context of the present invention and based on incipient wetting impregnation, on reflux boiling of the exchanging solution or fixed-bed percolation are preferred as they are both easy to effect and also extremely efficient.

With the incipient wetting impregnation technique, a preliminary drying is carried out at 105–120° C. under vacuum of the titanium silicalite, followed by the actual impregnation with a solution (not necessarily aqueous) with a volume equal to the pore volume of the catalyst and adequate content in the salt, either simple or complex, containing the cation(s) to be exchanged, after which it is filtered, washed with methanol, dried at 105–120° C. and calcined at 550° C. for 3–5 hours.

With the reflux boiling technique, the ion exchange is carried out by stirring the titanium silicalite in a solution of deionized water in which the salt containing the desired $M^{n+}$ cation(s) has been previously dissolved, not necessarily totally (in fact it is possible to use salts which are not very soluble, in which case there may be a certain suspension of the salt itself). The weight ratio between titanium silicalite and the salt solution (and/or suspension) is generally between 1:10 and 1:100, preferably between 1:5 and 1:30. The boiling point of the solution is maintained for a time generally ranging from 5 to 100 minutes, preferably between 15 and 50 minutes. After this period, the catalyst is filtered, washed with methanol and water, dried in an oven at 105–120° C. and calcined at 550° C. for 3–5 hours.

With the fixed-bed percolation technique, the salt solution and/or suspension (not necessarily aqueous) is percolated onto the catalyst to be treated contained in a jacketed tubular reactor. The eluate is recovered in a tank and recirculated with a pump to the reactor for as many times as is sufficient to exchange the established concentration of the cation (or cations) on the catalyst.

Alternatively, it is possible to percolate the solvent alone, which eluates a thin layer of the salt, containing the cation (or cations) to be exchanged, arranged on the upper part of the catalyst.

Also in this case, the percolate may, after the first passage, be conveniently recycled onto the catalyst. As an acidity of the protonic type is also exchanged in the process, the anion of the salt may be present in the eluate as conjugated acid of which analysis may provide a first indication of the concentration of the $M^{n+}$ cation (or cations) exchanged.

The catalyst is charged into the reactor in such a way as to obtain a pack which eliminates any preferential ways of the liquid through the solid with a consequent exchange homogeneity of the cation (or cations).

The ion exchange techniques described above refer to preventive neutralizations of the catalyst. The ion exchange process can, however, also be effected during the epoxidation reaction carried out in continuous by adding the saline agent to the fluid fed to the reactor, in a quantity varying according to the reaction medium, temperature, olefin to be epoxidated as well as the conversion rate to epoxide of the latter.

The high selectivity to epoxide which can be obtained in this way can therefore be advantageously maintained for the whole reaction period, as the salt continuously added with the feeding of the reagents can replace that possibly washed away by the catalyst, whereas the possible excess, remaining dissolved in the reaction medium, is automatically eliminated with the effluent solution from the epoxidation reactor. Under these conditions it is therefore possible to avoid or correct in a short time any possible drops in selectivity due to the re-establishment of the acidity of the titanium silicalite.

The quantity of $M^{n+}$ cation (or cations) which can be used in the preventive neutralization by ion exchange of the catalyst is between 0.0001% and 1%, preferably between 0.01% and 0.5% by weight with respect to the weight of the exchanging solution. If the treatment of the catalyst is carried out in continuous during the epoxidation reaction, the quantity of saline agent containing the cation is maintained at 0.0001% to 0.001% by weight with respect to the weight of the solution in the synthesis reactor.

If a previously treated catalyst is used in the epoxidation reaction, it may be advantageous, after a certain time, to re-establish the quantity of cation, possibly washed away, by integrating it with an appropriate quantity dissolved in the feeding to the synthesis reactor. This amount is generally quite small and is between 0.00001% and 0.0001% by weight with respect to the weight of the solution in the synthesis reactor.

Mainly with the last procedure described, it is possible to guarantee and maintain very high selectivities to epoxide already in the first phases of the reaction, without causing undesired reductions in the conversion rate to epoxide.

The catalyst which can be used in the process of the present invention is selected from those generally known as titanium silicalites which correspond to the general formula:

$$xTiO_2(1-x)SiO_2$$

wherein x is between 0.0001 and 0.15, preferably between 0.001 and 0.04. These materials are known in scientific literature and can be prepared according to the method described in U.S. Pat. No. 4,410,501 where their structural characteristics are also specified. Titanium silicalites in which part of the titanium is substituted by other metals such as boron, aluminum, iron or gallium, can also be used. These substituted titanium silicalites and their preparation methods are described in published European patent applications 226.257, 226.258 and 226.825.

The quantity of catalyst used in the process for the preparation of the epoxides of the present invention is not critical and is selected so as to allow the completion of the epoxidation reaction in as short a time as possible. The quantity of catalyst generally depends on the reaction temperature, reactivity and concentration of the olefins, the concentration of the hydrogen peroxide and type of solvent. For example, the quantity of catalyst can vary from 0.1 to 30 g per mole of olefin.

The olefinic compounds which can be used in the process of the present invention can be selected from organic compounds having at least one double bond and can be aromatic, aliphatic, alkylaromatic, cyclic, branched or linear. They are preferably olefinic hydrocarbons having from 2 to 30 carbon atoms in the molecule and containing at least one double bond.

Examples of olefins suitable for the purposes of the present invention are selected from those having the general formula:

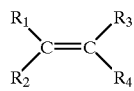

wherein: $R_1$, $R_2$, $R_3$, $R_4$, the same or different, can be H, an alkyl radical with from 1 to 20 carbon atoms, an aryl radical, an alkylaryl radical with from 6 to 20 carbon atoms, a cycloalkyl radical with from 6 to 10 carbon atoms, an alkylcycloalkyl radical with from 7 to 20 carbon atoms; the $R_1$, $R_2$, $R_3$ and $R_4$ radicals may form, in pairs, saturated or unsaturated rings. In addition, these radicals may contain halogen atoms, nitro, nitrile, sulfonic groups and relative esters, carbonyl, hydroxyl, carboxyl, thiol, amine groups and ethers.

Examples of olefins which can be epoxidated with the process of the present invention are: ethylene, propylene, allyl chloride, allyl alcohol, butenes, pentenes, hexenes, heptenes, octene-1, tridecene, mesityl oxide, isoprene, cyclo-octene, cyclohexene or bicyclic compounds such as norbornenes, pinenes, etc. The olefins may carry the above substituents on both unsaturated carbon atoms and different positions.

The oxidating agent used in the process of the present invention is hydrogen peroxide ($H_2O_2$) or a compound which under epoxidation conditions is capable of generating $H_2O_2$. The quantity of hydrogen peroxide with respect to the olefin is not critical, but it is preferable to use a molar ratio olefin/$H_2O_2$ ranging from 0.9 to 5, preferably between 0.95 and 3.

The epoxidation reaction can be carried out in one or more solvents liquid at epoxidation temperatures. Solvents of a polar nature such as alcohols (methanol, ethanol, isopropyl alcohol, t-butyl alcohol, cyclohexanol), ketones (for example acetone, methylethyl ketone, acetophenone), ethers (tetrahydrofuran, butyl ether), aliphatic and aromatic hydrocarbons, halogenated hydrocarbons, esters, glycols with a number of carbon atoms less than or equal to 6, aliphatic or aromatic nitriles (for example acetonitrile and benzonitrile), are typically used. Methanol and among the ketones, acetone, are preferably used.

The temperatures used in the process of the present invention generally range from 0 to 150° C., preferably from 20 to 100° C., more preferably from 30 to 80° C.

The operating pressures are those which enable the olefin to be maintained in the liquid phase at the temperature established for the reaction. The operating pressure is generally higher than atmospheric pressure when gaseous olefins are used.

The epoxidation process of the present invention can be carried out in batch, semi-continuous or, preferably, in continuous.

Different types of reactor can be used in the process of the present invention, for example, a fixed-bed reactor, a slurry reactor or a fluid-bed reactor. Depending on the type of reactor, the catalyst can be used in the form of microspheres, granules or tablets of various shapes and forms.

The process for the preparation of olefinic epoxides according to the present invention can be carried out using known methods. For example, all the reagents can be introduced into the reaction zone contemporaneously or in sequence. At the end of the epoxidation reaction the products can be separated and recovered from the reaction mixture using conventional techniques such as distillation, crystallization, liquid—liquid extraction, steam stripping, etc. The catalyst and also the non-reacted products (olefin and $H_2O_2$) can be recovered and re-used in subsequent epoxidation steps.

The following examples provide a better illustration of the invention without limiting its scope. The titanium silicalite used in the examples is prepared according to what is described in published European patent application 100.119. It is appropriately conserved in a dry or inert atmosphere. The total quantity of titanium silicalite measured with the FRX technique is equal to 2.05% by weight, whereas that resulting from chemical analysis is 2.02%.

EXAMPLE 1

100 g of titanium silicalite are suspended in 1000 ml of deionized water to which 8.4 g of basic zinc carbonate [$2ZnCO_3 \cdot 3Zn(OH)_2$] have been previously added.

The suspension is maintained, under adequate stirring, at reflux temperature for 30 minutes.

The catalyst thus treated is filtered, washed with boiling water and subsequently with methanol and is then dried in an oven at about 120° C. and calcined in muffle at 550° C. for 3 hours.

FRX analysis reveals [$Zn^{2+}$]=0.07% in the catalyst.

EXAMPLE 2

100 g of titanium silicalite are subjected to incipient wetting impregnation with 2.8 g of zinc acetate in a volume of solvent of 47 ml (the same as the pore volume of the catalyst), maintained at boiling point for 15 minutes.

The catalyst is then filtered, washed with boiling water and subsequently with methanol and is then dried in an oven at 120° C. and calcined in muffle at 550° C. for 3 hours.

FRX analysis reveals an incorporation of $Zn^{2+}$ equal to 0.066% in the catalyst.

EXAMPLE 3

100 g of packed titanium silicalite are charged into a jacketed pipe whose top is connected to a feeding tank of the eluant, maintained at a temperature of 80° C., which also acts as a tank for the recycling of the eluate.

4.4 g of zinc nitrate in the form of a fine layer are arranged on the top of the catalyst bed.

The solvent which eluates the fine layer is then percolated. After a first passage, the eluate is recycled to the feeding tank and the process is repeated for 60 minutes.

The catalyst thus exchanged is discharged from the pipe, washed with water and methanol and then dried at 120° C. and calcined at 550° C. for 5 hours.

FRX analysis reveals [$Zn^{2+}$]=0.06% in the catalyst.

EXAMPLE 4

100 of titanium silicalite are treated with 3.6 g of lanthanium acetate using the reflux boiling method for 30 minutes.

FRX analysis reveals an incorporation of $La^{3+}$ equal to 0.25% in the catalyst.

EXAMPLE 5

100 g of titanium silicalite are treated with 5.1 g of samarium nitrate using the fixed-bed percolation method for 40 minutes.

FRX analysis reveals a content of $Sm^{3+}$ incorporated in the catalyst of 0.28%.

EXAMPLE 6

100 of titanium silicalite are treated with 4.1 g of tallium nitrate using the reflux boiling method for 45 minutes.

FRX analysis reveals a content of $Tl^+$ exchanged in the catalyst equal to 0.15%.

EXAMPLE 7

100 g of titanium silicalite are treated with 3.1 g of cerium nitrate using the incipient wetting impregnation method for 30 minutes.

FRX analysis reveals a content of $Ce^{4+}$ exchanged in the catalyst equal to 0.32%.

EXAMPLE 8

100 g of titanium silicalite are treated contemporaneously with 4 g of calcium carbonate and 8 g of stronzium carbonate with the reflux boiling method for 50 minutes.

FRX analysis reveals an incorporation in the catalyst of 0.13% of $Sr^{2+}$ and 0.05% of $Ca^{2+}$.

In all the samples of titanium silicalite subjected to different cationic treatment the titers of titanium found were practically identical to those of the non-pretreated catalyst as revealed by DRX diffraction patterns.

EXAMPLE 9 (COMPARATIVE)

5 g of titanium silicalite as such (i.e. not treated with any of the salts of the invention) in 500 g of methanol are suspended in a 1 liter reactor, equipped with a mechanical stirrer with gaseous effect and a thermostatic system (internal coil immersed in the reaction solution and external circulation jacket)

After thermostat-regulating the system at 40° C. and pressurizing with propylene under stirring at 1.2 atms (constant for the whole duration of the test), 16.23 g of $H_2O_2$ at 34.74% by weight are added at such a rate as to exhaust the addition of the oxidating agent in 15 minutes.

After this period, a sample of reaction solution is immediately taken. The residual $H_2O_2$ is iodometrically determined whereas the reaction products are quantified by gaschromatography and HPLC. The results are:
conversion $H_2O2$: 96%;
selectivity to 1,2-epoxypropane: 93%;
yield of by-products (ethers+glycols): 6.5%.

EXAMPLE 10

An epoxidation test of propylene was carried out, adopting the same procedure and same quantities of reagents used in example 9, using however 5 g of titanium silicalite treated as specified in example 1. Analysis of the reaction sample effected after 15 minutes gives the following results:
conversion $H_2O2$: 97%;
selectivity to 1,2-epoxypropane: 98.2%;
yield of by-products (ethers+glycols): 1.5%.

EXAMPLE 11

The epoxidation of propylene is carried out under the same conditions as example 9, using 5 g of titanium silicalite treated as specified in example 2. After 15 minutes, analysis of the reaction sample gave the following results:
conversion $H_2O_2$: 96.6%;
selectivity to 1,2-epoxypropane: 98.5%;
yield of by-products (ethers+glycols): 1.2%.

EXAMPLE 12

The epoxidation of propylene is carried out adopting the same procedure as example 9, but using 5 g of titanium silicalite treated as specified in example 3. After 15 minutes, analysis of the reaction sample gave the following results:
conversion $H_2O_2$: 97.2%;
selectivity to 1,2-epoxypropane: 98.1%;
yield of by-products (ethers+glycols): 1.6%.

As can be noted, the performance of titanium silicalite treated with 3 different zinc salts is identical, proving that the effect is due to the cation and not to the accompanying anion.

EXAMPLE 13

400 g of methanol, 5 g of catalyst prepared as in example 2 and 40 g of allyl chloride are charged into the same reactor as example 9.

The solution is thermostat-regulated at 55° C. after which 28.2 g of $H_2O_2$ at 35.1% by weight are added over a period of 15 minutes. After a further 15 minutes, a reaction sample is removed which, after being subjected to iodometric, gaschromatographic and HPLC analyses, gives the following results:
conversion $H_2O_2$: 98.0%;
selectivity to 1-chloro-2,3-epoxypropane: 97.5%;
yield of by-products: 1.4%.

EXAMPLE 14 (COMPARATIVE)

The epoxidation of allyl chloride is carried out under the same conditions as example 13, but using 5 g of titanium silicalite as such.

The $H_2O_2$ is added in 15 minutes. After a further 15 minutes for completion, the results are as follows:
conversion $H_2O_2$: 96.3%;
selectivity to 1-chloro-2,3-epoxypropane: 92.8%;
yield of by-products: 6.3%.

EXAMPLE 15

400 g of methanol, 5 g of catalyst prepared as described in example 2 and 40 g of 1-octene are charged into the reactor used in the above experiments.

After thermostat-regulating the system at 60° C. under stirring, 23.3 g of $H_2O_2$ at 34.9% by weight are added in 15 minutes. After a further 30 minutes, the reaction sample is removed.

Iodometric, gaschromatographic and HPLC analyses give the following results:
conversion $H_2O_2$: 92.8%;
selectivity to 1,2-epoxyoctane: 92.0%;
yield of by-products (ethers+glycols): 5.8%.

EXAMPLE 16 (COMPARATIVE)

The epoxidation of 1-octene with non-treated titanium silicalite is carried out under the same conditions specified in example 15. The results obtained are:
conversion $H_2O_2$: 93.1%;
selectivity to 1,2-epoxyoctane: 97.5%;
yield of by-products (ethers+glycols): 2.1%.

EXAMPLE 17

Propylene is epoxidated under the same conditions as example 9, but using 5 g of titanium silicalite treated as specified in example 4.

After 15 minutes, analysis of the reaction sample indicates:
conversion $H_2O_2$: 97.3%;
selectivity to 1,2-epoxypropane: 97.1%;
yield of by-products: 2.3%.

EXAMPLE 18

Propylene is epoxidated under the same conditions as example 9, but using 5 g of titanium silicalite treated as specified in example 5.

After 15 minutes, a reaction sample is removed, whose analysis indicates:
conversion $H_2O_2$: 96.9%;
selectivity to 1,2-epoxypropane: 97.0%;
yield of by-products: 2.3%.

EXAMPLE 19

Propylene is epoxidated under the same conditions as example 9, using 5 g of titanium silicalite previously treated as indicated in example 6.

After 15 minutes, analysis of the reaction sample provides the following results:
conversion $H_2O_2$: 96.5%;
selectivity to 1,2-epoxypropane: 98.5%;
yield of by-products: 1.0%.

EXAMPLE 20

Propylene is epoxidated under the same operating conditions as example 9, with 5 g of titanium silicalite treated as specified in example 7.

Analyses carried out on a reaction sample after 15 minutes indicate:
conversion $H_2O_2$: 95.5%;
selectivity to 1,2-epoxypropane: 97.8%;
yield of by-products (ethers+glycols): 0.9%.

EXAMPLE 21

Propylene is epoxidated under the conditions specified in example 9, with 5 g of titanium silicalite previously treated as indicated in example 8.

After 15 minutes of reaction, analysis of a sample indicates:
conversion $H_2O_2$: 96.3%;
selectivity to 1,2-epoxypropane: 98.0%;
yield of by-products: 1.1%.

What is claimed is:

1. A process for the production of epoxides by the reaction of at least one olefin and hydrogen peroxide, or a compound capable of producing hydrogen peroxide under the reaction conditions, in the presence of a catalyst consisting of titanium silicalite subjected to ion exchange treatment (exchanged) with metal cations ($M^{n+}$) present on the catalyst in a quantity ranging from 0.01 to 1% by weight with respect to the total weight.

2. The process according to claim 1, wherein the metal cations are selected from those of group IIB; group IIIB; the rare-earth group, or lanthanides; vanadium; tungsten; tin and lead; indium and thallium and cations of group I and II, and ammonium.

3. The process according to claim 1 or 2, wherein the $M^{n+}$ cations are part of organic or inorganic salt complexes containing more than one of the cations of the above elements and in association with one or more of the elements selected from carbon, boron, silicon, nitrogen, phosphorous, sulfur, fluorine, selenium, arsenic, tin, molibden and antimonium.

4. The process according to claim 1, wherein the ion exchange is carried out by means of incipient wetting impregnation, reflux boiling of the exchanging solution or fixed-bed percolation techniques.

5. The process according to claim 1, wherein the titanium silicalites are selected from those have the general formula:

$$xTiO_2(1-x)SiO_2$$

wherein x is between 0.0001 and 0.15.

6. The process according to claim 5, wherein part of the titanium of the catalyst is substituted by another metal.

7. The process according to claim 1, wherein the catalyst is used in a quantity ranging from 0.1 to 30 g per mole of olefin.

8. The process according to claim 1, wherein the olefin is selected from hydrocarbons having from 2 to 30 carbon atoms in the molecule and containing at least one double bond.

9. The process according to claim 1, wherein the hydrogen peroxide is used in a molar ratio olefin/$H_2O_2$ ranging from 0.9 to 5.

10. The process according to claim 1, wherein the epoxidation reaction is carried out in one or more solvents liquid at the epoxidation temperatures.

11. The process according to claim 1, wherein the epoxidation temperatures range from 0 to 150° C.

12. The process according to claim 6, wherein the other metal is selected from the group consisting of boron, aluminum, iron and gallium.

13. The process according to claim 1, wherein the metal cation is a group IIB metal.

14. The process according to claim 13, wherein the group IIB metal is zinc.

15. The process according to claim 1, wherein the metal cation is a group IIIB metal.

16. The process according to claim 15, wherein the group IIIB metal is lanthanum.

17. The process according to claim 1, wherein the metal cation is a rare earth group metal.

18. The process according to claim 17, wherein the rare earth group metal is samarium.

19. The process according to claim 1, wherein the metal cation is vanadium.

20. The process according to claim 1, wherein the metal cation is tungsten.

21. The process according to claim 1, wherein the metal cation is tin.

22. The process according to claim 1, wherein the metal cation is lead.

23. The process according to claim 1, wherein the metal cation is indium.

24. The process according to claim 1, wherein the metal cation is thallium.

25. The process according to claim 1, wherein the metal cation is of group I or ammonium.

26. The process according to claim 1, wherein the metal cation is of group II.

* * * * *